United States Patent [19]

DiPietro et al.

[11] Patent Number: 5,047,549
[45] Date of Patent: Sep. 10, 1991

[54] DERIVATIVES OF PRAVASTATIN FOR INHIBITING CHOLESTEROL BIOSYNTHESIS

[75] Inventors: Richard A. DiPietro, North Brunswick; Jan-I Tu, Kendall Park; Noor Z. Turabi, Dayton, all of N.J.

[73] Assignee: E. R. Squibb & Sons, Inc., Princeton, N.J.

[21] Appl. No.: 338,816

[22] Filed: Apr. 17, 1989

Related U.S. Application Data

[62] Division of Ser. No. 171,092, Mar. 21, 1988, Pat. No. 4,857,522.

[51] Int. Cl.$^5$ .......................................... C07D 405/12
[52] U.S. Cl. .................................. 548/336; 540/596; 544/58.7; 544/149; 544/333; 544/405; 546/207; 546/268; 548/204; 548/214; 548/236; 548/300; 548/517; 549/60; 549/292; 424/1.1
[58] Field of Search ............... 540/596; 544/58.7, 149, 544/333, 405; 546/207, 268; 548/204, 214, 236, 300, 336, 517; 549/60, 292; 252/645; 424/1.1

[56] References Cited

U.S. PATENT DOCUMENTS 4,346,227 8/1982 Terahara ............................ 560/119

Primary Examiner—Mary C. Lee
Assistant Examiner—Patricia L. Morris
Attorney, Agent, or Firm—Burton Rodney

[57] ABSTRACT

Derivatives of pravastatin are provided which are useful in inhibiting cholesterol biosynthesis and in preparing radiolabeled compounds useful in the radioimmunoassay (RIA) of pravastatin and derivatives thereof. The pravastatin derivatives have the structure

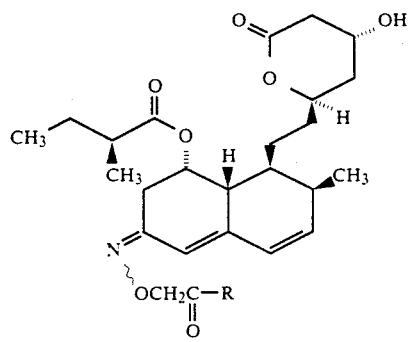

wherein R is hydroxy, lower alkylamine, arylamine, arylalkylamine or heterocyclic alkylamine such as histamine, tyramine, O-benzyltyramine, methyl tyrosinate as well as iodinated derivatives thereof.

3 Claims, No Drawings

DERIVATIVES OF PRAVASTATIN FOR INHIBITING CHOLESTEROL BIOSYNTHESIS

This is a division of application Ser. No. 171,092, filed Mar. 21, 1988, now U.S. Pat. No. 4,857,522.

FIELD OF THE INVENTION

The present invention relates to carboxymethyl oxime ether derivatives of pravastatin which may be employed as inhibitors of cholesterol synthesis, to hypocholesterolemic compositions containing such compounds, to a method for using such compounds accordingly, and to radiolabelled derivatives which may be employed in a radioimmunoassay of pravastatin.

BACKGROUND OF THE INVENTION

U.S. Pat. No. 4,346,227 to Terahara et al discloses inhibitors of cholesterol synthesis which includes pravastatin

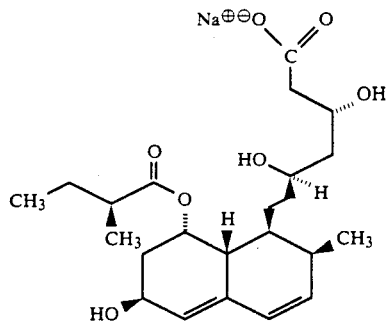

A specific radioimmunoassay (RIA) for pravastatin would require a radiolabelled derivative of pravastatin to act as a suitable antigen as well as a derivative which would bind to protein and thus act as an immunogen.

DESCRIPTION OF THE INVENTION

In accordance with the present invention, derivatives of pravastatin are provided which have the structure

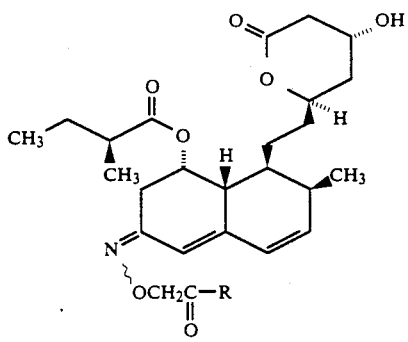

wherein R is hydroxy, lower alkylamine, arylamine, arylalkylamine or heterocyclic alkylamine or iodinated derivatives thereof, wherein the term heterocyclic includes 5-, 6- or 7-membered rings containing 1-, 2- or 3-heteroatoms such as N, 0 and/or S.

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkylaryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent or an alkylthio substituent.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, 1, 2 or 3 halogens (Cl, Br or F), 1, 2 or 3 lower alkoxy groups, 1, 2 or 3 hydroxy groups, 1, 2 or 3 phenyl groups, 1, 2 or 3 alkanoyloxy group, 1, 2 or 3 benzoyloxy groups, 1, 2 or 3 haloalkyl groups, 1, 2 or 3 halophenyl groups, 1, 2 or 3 allyl groups, 1, 2 or 3 cycloalkylalkyl groups, 1, 2 or 3 adamantylalkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, 1, 2 or 3 thiol groups, and/or 1, 2 or 3 alkylthio groups.

The term "aralkyl", "aryl-alkyl" or "aryl-lower alkyl" as used herein alone or as part of another group refers to lower alkyl groups as discussed above having an aryl substituent, such as benzyl.

The term heterocyclic alkyl as employed herein refers to 5-, 6- or 7-membered rings containing 1-, 2- or 3-hetero atoms which can be N, O and/or S, which are attached to an alkyl. Examples of such heterocyclic rings include, but are not limited to,

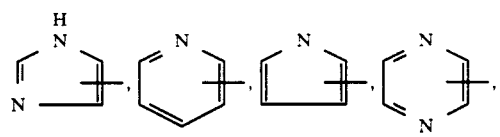

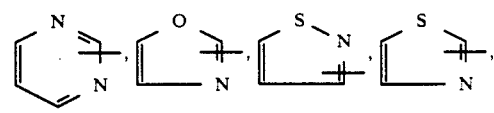

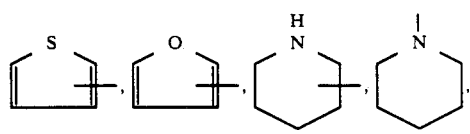

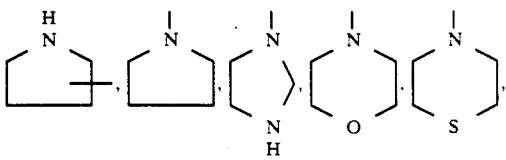

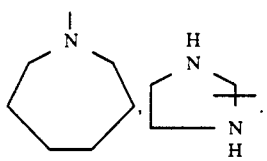

Preferred compounds of formula I of the invention are those where R is a heterocyclic alkylamine such as histamine, tyramine, O-benzyltyramine, methyl tyrosinate, 5-iodohistamine, methyl 3-iodotyrosinate or hydroxy.

The compounds of formula I of the invention may be prepared as follows.

Pravastatin is treated with a hydrogen donor such as N-hydroxysuccinimide, dichlorophenol or dinitrophenol, and an activating agent such as dicyclohexylcarbodiimide (DCC), 1-ethyl-3-(3-dimethylaminopropyl)carbodiimide HCl (EDAC), or diethylphosphonocyanidate (DEPC) in the presence of an organic solvent such as dimethylformamide, dioxane or tetrahydrofuran, to form the lactone A

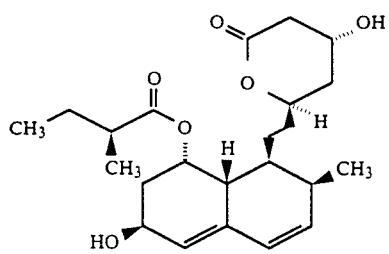

Lactone A is subjected to selective oxidation of the diallylic 3β-hydroxyl by treating lactone A with at least eight (8) equivalents of a deactivated chromium oxidizing agent, such as dimethylaminopyridine (DMAP)/-$CrO_3Cl^-$, or pyridinium chlorochromate (PCC), or chromium trioxide and pyridine (Collins reagent) in the presence of a halogenated solvent, such as chloroform, carbon tetrachloride or dichloroethane to form the dienone II

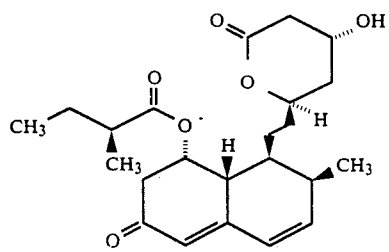

which is a novel intermediate.

Treatment of dienone II with carboxymethoxylamine in anhydrous protic organic solvent such as acetate buffered methanol affords the oxime ether III

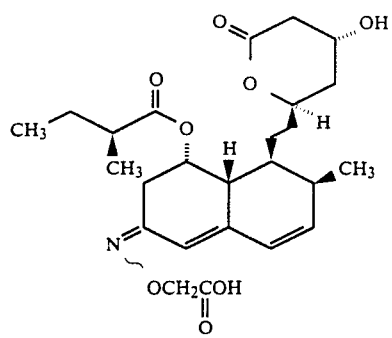

as an equimolar mixture of syn- and anti-isomers.

Compound III is a novel compound in accordance with the present invention.

Compound III may then be activated by treatment with N-hydroxysuccinimide in the presence of dicyclohexylcarbodiimide, oxalyl chloride or acetic anhydride and dimethylformamide. Without further purification, the reaction mixture is reacted with an amine B $R_1-NH_2$  B wherein $R_1$ is lower alkyl, aryl, arylalkyl or heterocyclic alkyl, or iodinated derivatives thereof in the presence of sodium phosphate buffer (pH 7-8) to form compounds of formula IV

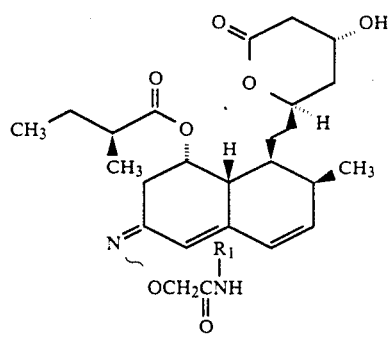

Radiolabelled compounds of the invention of the formula V

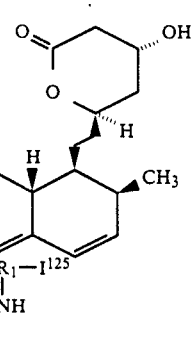

may be prepared by treating compound III with an activating agent such as N-hydroxysuccinimide in the presence of dicyclohexylcarbodiimide, oxalyl chloride or acetic anhydride and dimethylformamide and a radioiodinated amine C $^{125}I-R_1-NH_2$     C in the presence of sodium phosphate buffer (pH 7 to 8) to form V.

The iodinated amine C is known and/or may be prepared by conventional techniques, for example, by reacting amine B, preferably in the form of its dihydrochloride with radioactive iodine in the presence of a solvent such as ethanol while maintaining the pH at slightly alkaline levels with base such as sodium hydroxide.

The so-formed lactones of formula I may be hydrolyzed to the corresponding acid salt VI

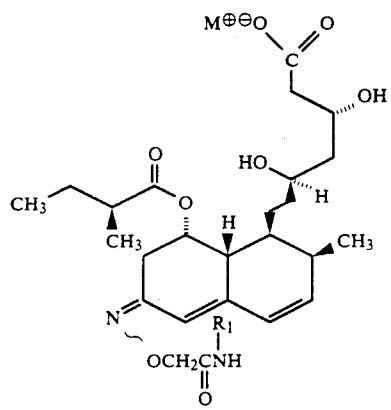

VI wherein M is an alkali metal such as sodium or potassium, or ammonium, by treating a solution of the lactone I in an inert organic solvent such as ethanol, methanol and the like with aqueous base such as aqueous sodium hydroxide or potassium hydroxide or ammonium hydroxide.

The compounds of the invention may be prepared as geometric mixtures and may later be resolved by conventional procedures to obtain the cis-isomer and trans-isomer. The pure isomer may return to a cis/trans mixture over time in solution.

The compounds of the invention are inhibitors of 3-hydroxy-3-methyl-glutaryl coenzyme A (HMG—CoA) reductase and thus are useful in inhibiting cholesterol biosynthesis as demonstrated by the following tests.

1) Rat Hepatic HMG-CoA Reductase

Rat hepatic HMG-CoA reductase activity is measured using a modification of the method described by Edwards (Edwards, P.A., et al., J. Lipid Res. 20:40, 1979). Rat hepatic microsomes are used as a source of enzyme, and the enzyme activity is determined by measuring the conversion of the $^{14}C$—HMG—CoA substrate to $^{14}C$-mevalonic acid.

a. Preparation of Microsomes

Livers are removed from 2-4 cholestyramine-fed, decapitated, Sprague Dawley rats, and homogenized in phosphate buffer A (potassium phosphate, 0.04 M, pH 7.2; KCl, 0.05 M; sucrose, 0.1 M; EDTA, 0.03 M; aprotinin, 500 KI units/ml). The homogenate is spun at $16,000 \times g$ for 15 minutes at 4° C. The supernatant is removed and recentrifuged under the same conditions a second time. The second $16,000 \times g$ supernatant is spun at $100,000 \times g$ for 70 minutes at 4° C. Pelleted microsomes are resuspended in a minimum volume of buffer A (3-5 ml per liver), and homogenized in a glass/glass homogenizer. Dithiothreitol is added (10 mM), and the preparation is aliquoted, quick frozen in acetone/dry ice, and stored at $-80°$ C. The specific activity of the first microsomal preparation was 0.68 nmole mevalonic acid/mg protein/minute.

b. Enzyme Assay

The reductase is assayed in 0.25 ml which contains the following components at the indicated final concentrations:

| | |
|---|---|
| 0.04M | Potassium phosphate, pH 7.0 |
| 0.05M | KCl |
| 0.10M | Sucrose |
| 0.03M | EDTA |
| 0.01M | Dithiothreitol |
| 3.5 mM | NaCl |
| 1% | Dimethylsulfoxide |
| 50-200 µg | Microsomal protein |
| 100 µM | $^{14}C$-[DL]HMG-CoA (0.05 µCi, 30-60 mCi/mmole) |
| 2.7 mM | NADPH (nicotinamide adenine dinucleotide phosphate) |

Reaction mixtures are incubated at 37° C. Under conditions described, enzyme activity increases linearly up to 300 µg microsomal protein per reaction mixture, and is linear with respect to incubation time up to 30 minutes. The standard incubation time chosen for drug studies is 20 minutes, which results in 12-15% conversion of HMG—CoA substrate to the mevalonic acid product. [DL—]HMG—CoA substrate is used at 100 µM, twice the concentration needed to saturate the enzyme under the conditions described. NADPH is used in excess at a level 2.7 times the concentration required to achieve maximum enzyme velocity.

Standardized assays for the evaluation of inhibitors are conducted according to the following procedure. Microsomal enzyme is incubated in the presence of NADPH at 37° C. for 15 minutes. DMSO vehicle with or without test compound is added, and the mixture further incubated for 15 minutes at 37° C. The enzyme assay is initiated by adding $^{14}C$—HMG—CoA substrate. After 20 minutes incubation at 37° C. the reaction is stopped by the addition of 25 µl of 33% KOH. $^3H$-mevalonic acid (0.05 µCi) is added, and the reaction mixture allowed to stand at room temperature for 30 minutes. Fifty µl 5N HCl is added to lactonize the mevalonic acid. Bromophenol blue is added as a pH indicator to monitor an adequate drop in pH. Lactonization is allowed to proceed for 30 minutes at room temperature. Reaction mixtures are centrifuged for 15 minutes at 2800 rpm. The supernatants are layered onto 2 grams AG 1-X8 anion exchange resin (Biorad, formate form) poured in 0.7 cm (ID) glass columns, and eluted with 2.0 ml $H_2O$. The first 0.5 ml is discarded, and the next 1.5 ml is collected and counted for both tritium and carbon 14 in 10.0 ml Opti-fluor scintillation fluid. Results are calculated as nmoles mevalonic acid produced per 20 minutes, and are corrected to 100% recovery of tritium. Drug effects are expressed as $I_{50}$ values (concentration of drug producing 50% inhibition of enzyme activity) derived from composite dose response data with the 95% confidence interval indicated.

Conversion of drugs in lactone form to their sodium salts is accomplished by solubilizing the lactone in DMSO, adding a 10-fold molar excess of NaOH, and allowing the mixture to stand at room temperature for 15 minutes. The mixture is then partially neutralized (pH 7.5-8.0) using 1N HCl, and diluted into the enzyme reaction mixture.

2) Cholesterol Synthesis in Freshly Isolated Rat Hepatocytes

Compounds which demonstrate activity as inhibitors of HMG-CoA reductase are evaluated for their ability to inhibit $^{14}$C-acetate incorporation into cholesterol in freshly isolated rat hepatocyte suspensions using methods originally described by Capuzzi et al. (Capuzzi, D.M. and Margolis, S., Lipids, 6:602, 1971).

a. Isolation of Rat Hepatocytes

Sprague-Dawley rats (180-220 grams) are anesthetized with Nembutol (50 mg/kg). The abdomen is opened and the first branch of the portal vein is tied closed. Heparin (100-200 units) is injected directly into the abdominal vena cava. A single closing suture is placed on the distal section of the portal vein, and the portal vein is cannulated between the suture and the first branching vein. The liver is perfused at a rate of 20 ml/minute with prewarmed (37° C.), oxygenated buffer A (HBSS without calcium or magnesium containing 0.5 mM EDTA) after severing the vena cava to allow drainage of the effluent. The liver is additionally perfused with 200 ml of prewarmed buffer B (HBSS containing 0.05% bacterial collagenase). Following perfusion with buffer B, the liver is excised and decapsulated in 60 ml Waymouth's medium allowing free cells to disperse into the medium. Hepatocytes are isolated by low speed centrifugation for 3 minutes at 50×g at room temperature. Pelleted hepatocytes are washed once in Waymouth's medium, counted and assayed for viability by trypan blue exclusion. These hepatocyte enriched cell suspensions routinely show 70-90% viability.

b. $^{14}$C-Acetate Incorporation into Cholesterol

Hepatocytes are resuspended at 5×10$^6$ cells per 2.0 ml in incubation medium (IM) [0.02 M Tris-HCl (pH 7.4), 0.1 M KCl, 3.3 mM sodium citrate, 6.7 mM nicotinamide, 0.23 mM NADP, 1.7 mM glucose-6-phosphate].

Test compounds are routinely dissolved in DMSO or DMSO:H$_2$O (1:3) and added to the IM. Final DMSO concentration in the IM is $\leq$1.0%, and has no significant effect on cholesterol synthesis.

Incubation is initiated by adding $^{14}$C-acetate (58 mCi/mmol, 2 μCi/ml), and placing the cell suspensions (2.0 ml) in 35 mm tissue culture dishes, at 37° C. for 2.0 hours. Following incubation, cell suspensions are transferred to glass centrifuge tubes and spun at 50×g for 3 minutes at room temperature. Cell pellets are resuspended and lysed in 1.0 ml H$_2$O, and placed in an ice bath.

Lipids are extracted essentially as described by Bligh, E. G. and W. J. Dyer, Can. J. Biochem. and Physiol., 37:911, 1959. The lower organic phase is removed and dried under a stream of nitrogen, and the residue resuspended in (100 μl) chloroform:methanol (2:1). The total sample is spotted on silica gel (LK6D) thin-layer plates and developed in hexane:ethyl ether:acetic acid (75:25:1). Plates are scanned and counted using a BioScan automated scanning system. Radiolabel in the cholesterol peak (RF 0.28) is determined and expressed as total counts per peak and as a percent of the label in the total lipid extract. Cholesterol peaks in control cultures routinely contain 800-1000 cpm, and are 9-20% of the label present in the total lipid extract; results compatible with Capuzzi, et al., indicating 9% of extracted label in cholesterol.

Drug effects (% inhibition of cholesterol synthesis) are determined by comparing % of label in cholesterol for control and drug treated cultures. Dose response curves are constructed from composite data from two or more studies, and results are expressed as I$_{50}$ values with a 95% confidence interval.

3) Cholesterol Synthesis in Human Skin Fibroblasts

Compound selectivity favoring greater inhibitory activity in hepatic tissue would be an attribute for a cholesterol synthesis inhibitor. Therefore, in addition to evaluating cholesterol synthesis inhibitors in hepatocytes, these compounds are also tested for their activity a inhibitors of cholesterol synthesis in cultured fibroblasts.

a. Human Skin Fibroblast Cultures

Human skin fibroblasts (passage 7-27) are grown in Eagles' minimal essential medium (EM) containing 10% fetal calf serum. For each experiment, stock cultures are trypsinized to disperse the cell monolayer, counted, and plated in 35 mm tissue culture wells (5×10$^5$ cells/2.0 ml). Cultures are incubated for 18 hours at 37° C. in 5% CO$_2$/95% humidified room air. Cholesterol biosynthetic enzymes are induced by removing the serum containing medium, washing the cell monolayers, and adding 1.0 ml of EM containing 1.0% fatty acid free bovine serum albumin, and incubating the cultures an additional 24 hours.

b. $^{14}$C-Acetate Incorporation into Cholesterol

Induced fibroblast cultures are washed with EMEM$_{100}$ (Earle's minimal essential medium). Test compounds are dissolved in DMSO or DMSO:EM (1:3) (final DMSO concentration in cell cultures $\leq$1.0%), added to the cultures, and the cultures preincubated for 30 minutes at 37° C. in 5% CO$_2$/95% humidified room air. Following preincubation with drugs, [1-$^{14}$C]Na acetate (2.0 μCi/ml, 58 mCi/mmole) is added, and the cultures reincubated for 4 hours. After incubation, the culture medium is removed, and the cell monolayer (200 μg cell protein per culture) is scraped into 1.0 ml of H$_2$O. Lipids in the lysed cell suspension ar extracted into chloroform:methanol as described for hepatocyte suspensions. The organic phase is dried under nitrogen, and the residue resuspended in chloroform:methanol (2:1) (100 μl), and the total sample spotted on silica gel (LK6D) thin-layer plates, and analyzed as described for hepatocytes.

Inhibition of cholesterol synthesis is determined by comparing the percent of label in the cholesterol peak from control and drug-treated cultures. Results are expressed as I$_{50}$ values, and are derived from composite dose response curves from two or more experiments. A 95% confidence interval for the I$_{50}$ value is also calculated from the composite dose response curves.

A further aspect of the present invention is a pharmaceutical composition consisting of at least one of the compounds of formula I in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations, such dosage forms containing from 1 to 2000 mg of active compound per dosage, for use in the treatment. The dose to be administered depends on the unitary dose, the symptoms, and the age and the body weight of the patient.

The compounds of formula I may be administered in a similar manner as known compounds suggested for use in inhibiting cholesterol biosynthesis, such as lovastatin, in mammalian species such as humans, dogs, cats and the like. Thus, the compounds of the invention may be administered in an amount from about 4 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The following Examples represent preferred embodiments of the present invention. All temperatures are expressed in degrees Centigrade unless otherwise indicated.

All reported yields represent isolated pure material. All compounds were satisfactorily characterized by $^1$H NMR, MS, IR, HPLC, TLC and elemental analysis (C,H,N ±0.4%).

EXAMPLE 1

[1S[1<a(R*),7<b(2S*,4S*),8a<b]]-2-Methylbutanoic acid, 3-(carboxymethyl)imino]-1,2,3,7,8,8a-hexahydro-7-methyl-8-[2-(tetrahydro-4-hydroxy-6-oxo-2H-pyran-2-yl)ethyl]-1-naphthalenyl ester

A.

[1S-[1<a(R*),7<b(2S*,4S*),8a<b]]-2-Methylbutanoic acid, 1,2,3,7,8,8a-hexahydro-3-hydroxy-7-methyl-8-[2-(tetrahydro-4-hydroxy-6-oxo-2H-pyran-2-yl)ethyl]-1-naphthalenyl ester To a dry 100 ml round-bottomed flask equipped with a stir bar and CaSO$_4$ drying tube was added 3.32 g (7.44 mmol) of pravastatin, 3.47 g (16.8 mmol) of dicyclohexylcarbodiimide (DCC), 1.93 g (16.8 mmol) of N-hydroxysuccinimide and 50 ml of dry dimethylformamide (DMF) (distilled from CaO) and the mixture stirred at room temperature for 16 hours. The resulting suspension was filtered and the filtrate evaporated at 30° C under reduced pressure. The residue was taken up in 50 ml of 20:1 CHCl$_3$:MeOH, filtered and evaporated. The resulting yellow oil was applied to 300 g of silica gel and eluted in a stepwise manner (1 liter of 40:1 CHCl$_3$:MeOH; 1 liter of 30:1 CHCl$_3$:MeOH, 1 liter of 20:1 CHCl$_3$:MeOH). The product was eluted with the 20:1 eluant. The good fractions (TLC, 8:1 CHCl$_3$ isopropyl alcohol (IPA) were combined and evaporated and the resulting oil triturated with ether to yield 2.15 g (71%) of the title compound as a white powder.

B.

[1S-[1<a(R*),7<b(2S*,4S*),8a<b]]-2-Methylbutanoic acid, 1,2,3,7,8,8a-hexahydro-7-methyl-3-oxo-8-[2-(tetrahydro-4-hydroxy-6-oxo-2H-pyran-2-yl)-ethyl]-1-naphthalenyl ester To a dry 500 ml round-bottomed flask equipped with a stir bar and a CaSO$_4$ drying tube was added 1.0 g (2.33 mmol) of the Part A lactone, 5.1 g (19.7 mmol) of CrO$_3$Cl-dimethylaminopyridine (DMAP) and 250 ml of CHCl$_3$ and the mixture stirred for 18 hours at room temperature protected from light. The dark suspension was then filtered over a bed of Celite and the filtrate evaporated at room temperature under reduced pressure. The resulting dark oil was applied to 200 g of silica gel and eluted slowly with 9:1 CHCl$_3$:IPA (the column was protected from light). The good fractions (TLC, 9:1 CHCl$_3$:IPA) were combined and evaporated to a slightly yellow oil which was triturated with pentane to yield 255 mg (27%) of the title compound as a white powder. This material rapidly takes up water to become the title hemihydrate.

C.

[1S-[1<a(R*),7<b(2S*,4S*),8a<b]]-2-Methylbutanoic acid, 3-[(carboxymethyl)-imino]-1,2,3,7,8,8a-hexahydro-7-methyl-8-[2-(tetrahydro-4-hydroxy-6-oxo-2H-pyran-2-yl)ethyl]-1-naphthalenyl ester To a 50 ml round-bottomed flask equipped with a stir bar and drying tube was added 178 mg (0.44 mmol) of Part B dienone, 340 mg (1.54 mmol) of carboxymethoxylamine hemihydrochloride, 133 mg (1.62 mol) of sodium acetate (anhyd.), 30 ml of MeOH (abs.), and 15 drops of HOAc (glacial) and the mixture stirred at room temperature for 18 hours. The mixture was then poured into 125 ml of 5:1 CHCl$_3$:MeOH and washed 4×40 ml with H$_2$O. The organic solution was dried over MgSO$_4$, filtered, and evaporated to an oil which was applied to 110 g of silica gel and eluted slowly with 6:1:0.2 CHCl$_3$:IPA:acetic acid. The good fractions were pooled and evaporated under reduced pressure at room temperature. The resulting oil was co-evaporated with 2 volumes of cyclohexene to yield, after drying in vacuo, 116 mg (55%) of the title compound.

EXAMPLE 2

[1S-[1<a(R*),7<b,8<b(2S*,4S*),8a<b]]-2-Methylbutanoic acid, 1,2,3,7,8,8a-hexahydro-3-[[2-[[2-(1H-imidazol-4-yl)ethyl]amino]-2-oxoethoxy]imino]7-methyl-8-[2-(tetrahydro-4-hydroxy-6-oxo-2H-pyran-2-yl)ethyl]-1-naphthalenyl ester To a dry 10 ml round-bottomed flask equipped with a stir bar and drying tube was added 100 mg (0.21 mmol) of Example 1 compound, 54.5 mg (0.47 mmol) of N-hydroxysuccinimide, 97.6 mg (0.47 mmol) of dicyclohexylcarbodiimide (DCC), and 6 ml of dry DMF (distilled from BaO). The mixture was stirred at room temperature for 2 hours at which time 69.8 mg (0.63 mmol) of histamine in 2 ml of pH 7.5 phosphate buffer was added in one portion and the mixture stirred for an additional 2 hours. The mixture was then evaporated on a rotary evaporator and the resulting residue taken up in 3:1 CHCl$_3$:MeOH and filtered. The filtrate was reduced in volume and chromatographed on silica gel (eluant: 3:1, CHCl$_3$:MeOH). The best fractions were pooled and evaporated to yield, after drying in vacuo, 60 mg (50%) of the title compound as an amorphous powder.

EXAMPLE 3

[1S-[1<a(R*),7<b(2S*,4S*),8a<b]]-2-Methylbutanoic acid,
  1,2,3,7,8,8a-hexahydro-3-[[2-(5-iodo-1H-imidazol-4-yl)ethyl]amino]-2-oxoethoxy]imino]-7-methyl-8-[2-(tetrahydro-4-hydroxy-6-oxo-2H-pyran-2-yl)ethyl]-1-naphthalenyl ester ($^{127}$I-Iodohistamine Conjugation)

A. 5-Iodohistamine dihydrochloride

To a 250 ml round-bottomed flask equipped with a stir bar and addition funnel was added 4.0 g (21.7 mmol) of histamine dihydrochloride and 6.0 ml of distilled water and the pH adjusted to 8.0 with concentrated NaOH. The addition funnel was charged with a solution of 2.76 g (10.86 mmol, 0.5 equivalent) of $I_2$ in 100 ml of ethanol (abs.) and the solution added slowly dropwise with stirring at room temperature over 6 hours. The pH was periodically monitored and maintained at an apparent pH=8.0 with concentrated NaOH. The dark suspension was then stirred overnight, readjusted to pH=8.0 and allowed to stir an additional 3 hours. The suspension was filtered and evaporated to a red oil. Purification of this material was accomplished by electrophoresis using a 1M HOAc buffer titrated to pH 5 with pyridine. Approximately 400 mg of crude material, dissolved in methanol, was applied in a 1 cm band to an 8"×16" paper which was run for 1 hour at 20 V/cm and 150-180 mA. A thin strip was then removed from the paper and visualized with ninhydrin spray. The iodohistamine band was then cut out of the remaining sheet and eluted with several portions of methanol. The methanol extracts were acidified (con.HCl) and evaporated in vacuo. The remaining residue was re-evaporated with one volume of absolute ethanol followed by recrystallization from absolute ethanol. In this manner 620 mg (19%) of the analytically pure title compound was isolated, m.p. 210° C. with decomposition. The mother liquor was pooled, evaporated, and the residue recrystallized to yield an additional 205 mg of somewhat inferior material.

B.
[1S-[1<a(R*),7<b(2S*,4S*),8a<b]]-2-Methylbutanoic acid,
  1,2,3,7,8,8a-hexahydro-3-[[2-(5-iodo-1H-imidazol-4-yl)ethyl]amino]-2-oxoethoxy]imino]-7-methyl-8-[2-(tetrahydro-4-hydroxy-6-oxo-2H-pyran-2-yl)ethyl]-1-naphthalenyl ester ($^{127}$I-Iodohistamine Conjugation)

To a dry 10 ml round-bottomed flask equipped with a stir bar and drying tube was added 100 mg (0.21 mmol) of Example 1 compound, 54.5 mg (0.48 mmol) of N-hydroxysuccinimide, 97.6 mg (0.48 mmol) of dicyclohexylcarbodiimide and 6 ml of dry DMF (distilled from BaO). The mixture was stirred at room temperature for 2.5 hours at which time 91 mg (0.29 mmol) of 5-iodohistamine dihydrochloride in 3 ml of 0.5M phosphate buffer (pH=7.4) was added in one portion with vigorous stirring. The mixture was stirred overnight at room temperature. The resulting suspension was filtered (precipitated dicyclohexylurea), the filtrate evaporated at reduced pressure and the residue chromatographed on silica gel (eluant: 9:1 CHCl$_3$:MeOH). The best fractions were pooled and evaporated to yield, after drying in vacuo, 78 mg (53%) of the title compound as an amorphous powder.

EXAMPLE 4

[1S-[1<a(R*),7<b,8<b(2S*,4S*),8a<b]]-2-Methylbutanoic acid,
  1,2,3,4,8,8a-hexahydro-7-methyl-3-[[2-[[2-[4-phenylmethoxy)phenyl]ethyl]amino]-2-oxoethoxy]imino]-8-[2-(tetrahydro-4-hydroxy-6-oxo-2H-pyran-2-yl)ethyl]-1-naphthalenyl ester To a dry 25 ml round-bottomed flask equipped with a stir bar and drying tube was added 50 mg (0.11 mmol) of Example 1 compound, 30.2 mg (0.26 mmol) of N-hydroxysuccinimide, 52 mg (0.25 mmol) of dicyclohexylcarbodiimide and 10 ml of dry DMF (distilled from BaO). The mixture was stirred at room temperature for 2.5 hours at which time 72 mg (0.31 mmol) of O-benzyl tyramine was added in one portion with vigorous stirring. The mixture was stirred overnight at room temperature. The resulting suspension was filtered (precipitated dicyclohexylurea), the filtrate evaporated at reduced pressure and the residue chromatographed by reversed-phase preparative HPLC. The best fractions were pooled and evaporated to yield, after drying in vacuo, the title compound as an amorphous white powder, 38 mg (53% yield).

EXAMPLE 5

[1S-[1<a(R*),3(R*),7<b,8<b(2S*,4S*),8a<b]]-2Methylbutanoic acid,
  1,2,3,7,8,8a-hexahydro-3-[[2-[[1-[(4-hydroxy-3-iodophenyl)methyl]-2-methoxy-2-oxoethyl]amino]-2-oxoethoxy]imino]-7-methyl-8-[2-(tetrahydro-4-hydroxy-6-oxo-2H-pyran-2-yl)ethyl]-1-naphthalenyl ester To a dry 25 ml round-bottomed flask equipped with a stir bar and drying tube was added 50 mg (0.11 mmol) of Example 1 compound, 27.2 mg (0.24 mmol) of N-hydroxysuccinimide, 48.8 mg (0.24 mmol) of dicyclohexylcarbodiimide and 6 ml of dry DMF (distilled from BaO). The mixture was stirred at room temperature for 2.5 hours at which time 112 mg (0.31 mmol) of methyl 3-iodo-tyrosinate hydrochloride in 3 ml of DMF containing 50 μl of triethylamine was added in one portion with vigorous stirring. The mixture was stirred overnight at room temperature. The resulting suspension was filtered (precipitated dicyclohexylurea), the filtrate evaporated at reduced pressure and the residue chromatographed on silica gel (eluant: 9:1 CHCl$_3$:MeOH). The best fractions were pooled and evaporated to yield, after drying in vacuo, the title compound as an amorphous white powder, 30.7 mg (37% yield).

EXAMPLE 6

[1S-[1<a(R*),7<b,8<b(2S*,4S*),8a<b]]-2-Methylbutanoic acid,
  1,2,3,7,8,8a-hexahydro-3-[[2-[2-(4-hydroxyphenyl)ethyl)amino]-2-oxoethoxy]-imino]-7-methyl-8-[2-(tetrahydro-4-hydroxy-6-oxo-2H-pyran-2-yl)ethyl]-1-naphthalenyl ester To a dry 25 ml round-bottomed flask equipped with a stir bar and drying tube was added 50 mg (0.11 mmol) of Example 1 compound, 27.2 mg (0.24 mmol) of N-hydroxysuccinimide, 48.8 mg (0.24 mmol) of dicyclohexylcarbodiimide and 6 ml of dry DMF (distilled from BaO). The mixture was stirred at room temperature for 2.5 hours at which time 43.2 mg (0.31 mmol) of tyramine in a mixture of 4 ml of DMF and 1.5 ml of 0.5 M phosphate buffer (pH=7.4) was added in one portion with vigorous stirring. The mixture was stirred for 3 hours at room temperature. The resulting suspension was filtered (precipitated dicyclohexylurea), the filtrate evaporated at reduced pressure and the residue chromatographed on silica gel (eluant: 9:1 CHCl₃:MeOH). The best fractions were pooled and evaporated to yield, after drying in vacuo, the title compound as an amorphous white powder, 25 mg (40% yield).

EXAMPLE 7

[1S-[1<a(R*),3(R*),7<b,8<b(2S*,4S*),8a<b]]-2-Methylbutanoic acid, 1,2,3,7,8,8a-hexahydro-3-[2-[[1-(4-hydroxyphenyl)methyl]-2-methoxy-2-oxoethyl]-amino]-2-oxoethoxy]imino]-7-methyl-8-[2-(tetrahydro-4-hydroxy-6-oxo-2H-pyran-2-yl)ethyl]-1-naphthalenyl ester To a dry 25 ml round-bottomed flask equipped with a stir bar and drying tube was added 50 mg (0.11 mmol) of Example 1 compound, 27.2 mg (0.24 mmol) of N-hydroxysuccinimide, 48.8 mg (0.24 mmol) of dicyclohexylcarbodiimide and 6 ml of dry DMF (distilled from BaO). The mixture was stirred at room temperature for 2.5 hours at which time 72.8 mg (0.31 mmol) of tyrosine methyl ester hydrochloride in 0.5 ml of 0.5 M phosphate buffer (pH=7.4) and 0.5 ml of DMF were added in one portion with vigorous stirring. The mixture was stirred for 3 hours at room temperature. The resulting suspension was filtered (precipitated dicyclohexylurea), the filtrate evaporated at reduced pressure and the residue chromatographed on silica gel. The best fractions were pooled and evaporated to yield, after drying in vacuo, the title compound as an amorphous white powder, 27 mg (40% yield).

EXAMPLE 8

Hydrolysis of Lactone of (3R,5R)-3,5-dihydroxy-7[1S,2S,8S,8aR-1,2,7,8-tetrahydro-2-methyl-6-[(carboxymethyl)imino]-8-[(S)-2-methyl-1-oxobutoxy]-1-naphthalenyl]-heptanoic acid, diammonium salt To a 10 ml round-bottomed flask is added 10 mg of Example 1 lactone dissolved in 0.5 ml of ethanol. Exactly 2.1 equivalents of NH₄OH dissolved in 1.0 ml of H₂O is added in one portion and the mixture stirred for 6 hours at 37° C. The solution is diluted with 5 ml of H₂O and extracted 3×5 ml with CHCl₃. The aqueous layer is separated and lyophilized to yield the ammonium salt of the free acid as a hygroscopic white powder.

It will also be appreciated that salts of the free acids of any of the lactones of Examples 2 to 7 may be prepared by treating the lactone with hydroxide as described in Example 8.

What is claimed is:

1. A radiolabelled compound for use in the radioimmunoassay of pravastatin, said compound having the structure

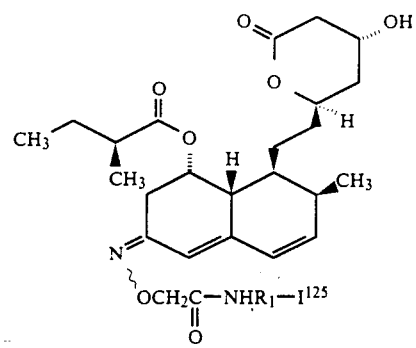

wherein $R_1$ is lower alkyl, aryl, arylalkyl or heterocyclic alkyl wherein the term "heterocyclic alkyl" refers to a 5, 6- or 7-membered ring containing 1- or 2-hetero atoms which are N, O and/or S, which ring is attached to an alkyl, said heterocyclic being

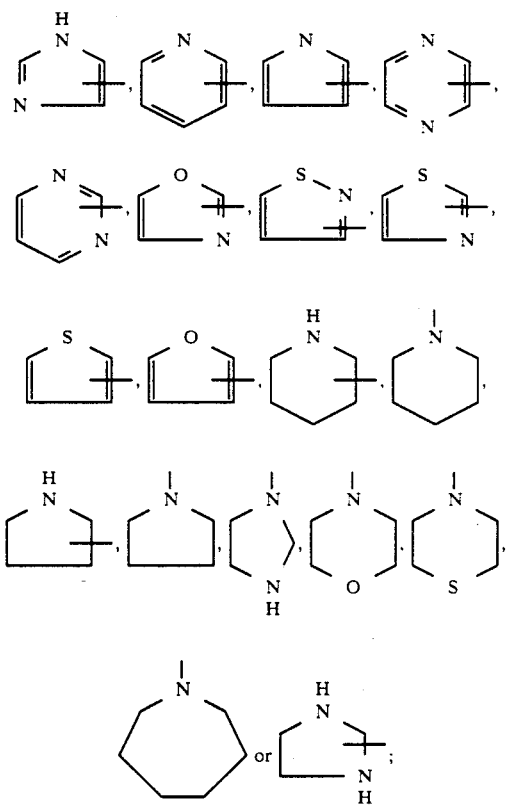

the term "aryl" by itself or as part of an arylalkyl group refers to a substituted or unsubstituted monocyclic or bicyclic aromatic hydrocarbon group containing from 6 to 10 carbons in the ring; and the term "lower alkyl" and "alkyl" by itself or as part of another group is substituted or unsubstituted and contains 1 to 12 carbons in the normal chain, wherein the substituent on the lower alkyl or alkyl group is a halo-substituent, $CF_3$, an alkoxy substituent, an aryl substituent, an alkyl-aryl substituent, a haloaryl substituent, a cycloalkyl substituent, an alkyl-cycloalkyl substituent, hydroxy, an alkylamino substituent, an alkanoylamino substituent, a cyano substituent, a thiol substituent or an alkylthio substituent, and wherein the substituent on the monocyclic or bicyclic aromatic hydrocarbon group is 1 2 or 3 lower alkyl groups, 1, 2 or 3 halogens (Cl, Br or F), 1, 2 or 3 lower alkoxy groups, 1, 2 or 3 hydroxy groups, 1, 2 or 3 phenyl groups, 1, 2 or 3 alkanoyloxy groups, 1, 2 or 3 benzoyloxy groups, 1, 2 or 3 haloalkyl groups, 1, 2 or 3 halophenyl groups, 1, 2 or 3 allyl groups, 1, 2 or 3 cycloalkylalkyl groups, 1, 2 or 3 adamantylalkyl groups, 1, 2 or 3 alkylamino groups, 1, 2 or 3 alkanoylamino groups, 1, 2 or arylcarbonylamino groups, 1, 2 or 3 amino groups, 1, 2 or 3 nitro groups, 1, 2 or 3 cyano groups, 1, 2 or 3 thiol groups, and/or 1, 2 or 3 alkylthio groups.

2. The compound as defined in claim 1 wherein $R_1$ is

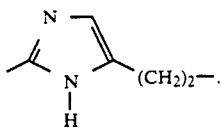

3. The compound as defined in claim 1 wherein $R_1$ is

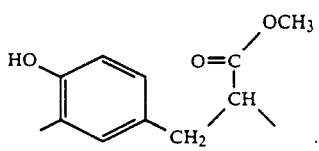

* * * * *

UNITED STATES PATENT AND TRADEMARK OFFICE
CERTIFICATE OF CORRECTION

PATENT NO. : 5,047,549

DATED : September 10, 1991

INVENTOR(S) : Richard A. DiPietro, Jan-I Tu and Noor Z. Turabi

It is certified that error appears in the above-identified patent and that said Letters Patent is hereby corrected as shown below:

Column 14, Line 65, insert the following after
an alkanoylamino substituent,:

-- an arylcarbonylamino substituent, a nitro substituent, --

Signed and Sealed this

Twenty-ninth Day of December, 1992

Attest:

DOUGLAS B. COMER

*Attesting Officer*   Acting Commissioner of Patents and Trademarks